(12) United States Patent
Vatenos

(10) Patent No.: US 9,684,765 B2
(45) Date of Patent: Jun. 20, 2017

(54) SYSTEMS AND METHODS FOR REMOTE IDENTIFICATION

(71) Applicant: RMS Omega Technologies, Baltimore, MD (US)

(72) Inventor: Peter Michael Vatenos, Fallston, MD (US)

(73) Assignee: RMS Omega Technologies Group, Inc, Bluffton, SC (US)

( * ) Notice: Subject to any disclaimer, the term of this patent is extended or adjusted under 35 U.S.C. 154(b) by 0 days.

(21) Appl. No.: 14/725,738

(22) Filed: May 29, 2015

(65) Prior Publication Data

US 2016/0350493 A1 Dec. 1, 2016

(51) Int. Cl.
*G06F 19/00* (2011.01)
*G06K 7/10* (2006.01)
*G06K 19/077* (2006.01)
*G06K 17/00* (2006.01)

(52) U.S. Cl.
CPC ....... *G06F 19/323* (2013.01); *G06K 7/10366* (2013.01); *G06K 19/07758* (2013.01); *G06K 2017/009* (2013.01)

(58) Field of Classification Search
CPC ............ G08B 13/1427; G08B 21/0219; G08B 21/0255; G08B 21/22; G06F 19/327; G06F 19/323; G06F 19/3406; A61G 7/05; A61G 2203/16; G06K 7/10; G06K 19/07762; G06K 19/07758; G06K 2017/009; G06K 7/10366; H04W 4/00; A61B 5/117; A61B 5/0024
USPC ........................ 340/10.1, 539.12, 5.61, 10.51
See application file for complete search history.

(56) References Cited

U.S. PATENT DOCUMENTS

2012/0056719 A1* 3/2012 Krishna ........... G06K 19/07762
340/10.1
2014/0240088 A1* 8/2014 Robinette ............ G08B 13/1427
340/5.61

* cited by examiner

*Primary Examiner* — Ali Neyzari

(57) ABSTRACT

Improved systems and methods are described for improving patient care, safety, and workflow. In particular, a rewritable identification device is provided. In some examples, identification data is exchanged between an identification device and a bidirectional device. At the outset, the identification device may receive a request for identification data from the bidirectional device. In response to the request, the identification device may retrieve the requested identification data as well as supplemental data associated with the identification data. After retrieval, the identification device may transmit, within an ultra-high frequency range, a radio frequency identification tag containing the requested identification data and the supplemental data to the bidirectional device.

27 Claims, 7 Drawing Sheets

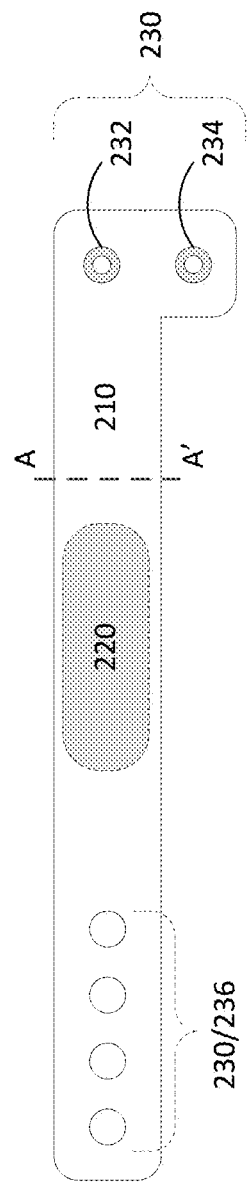

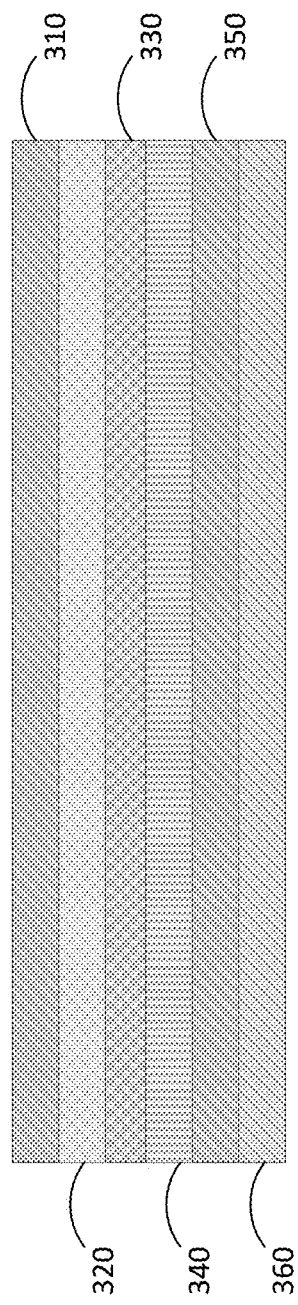

500

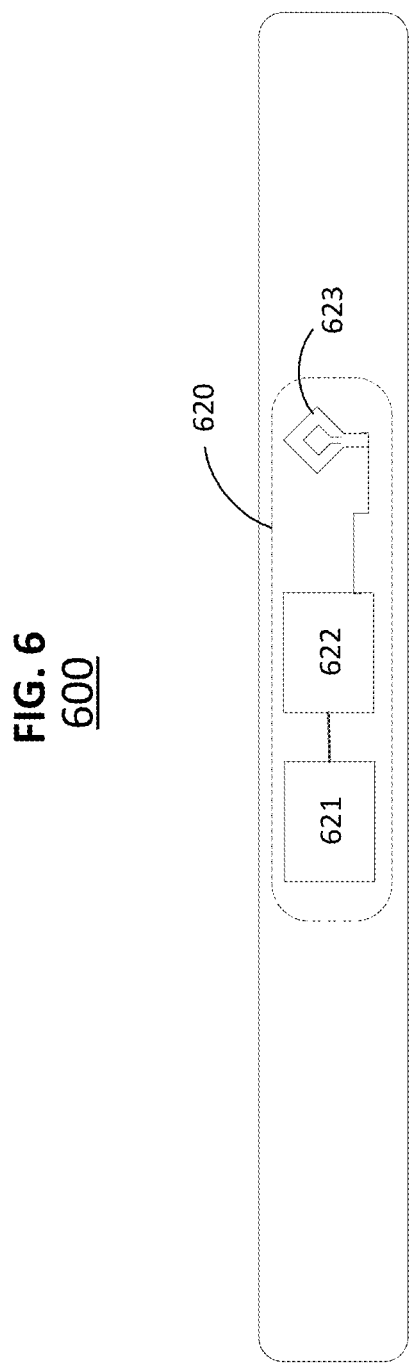

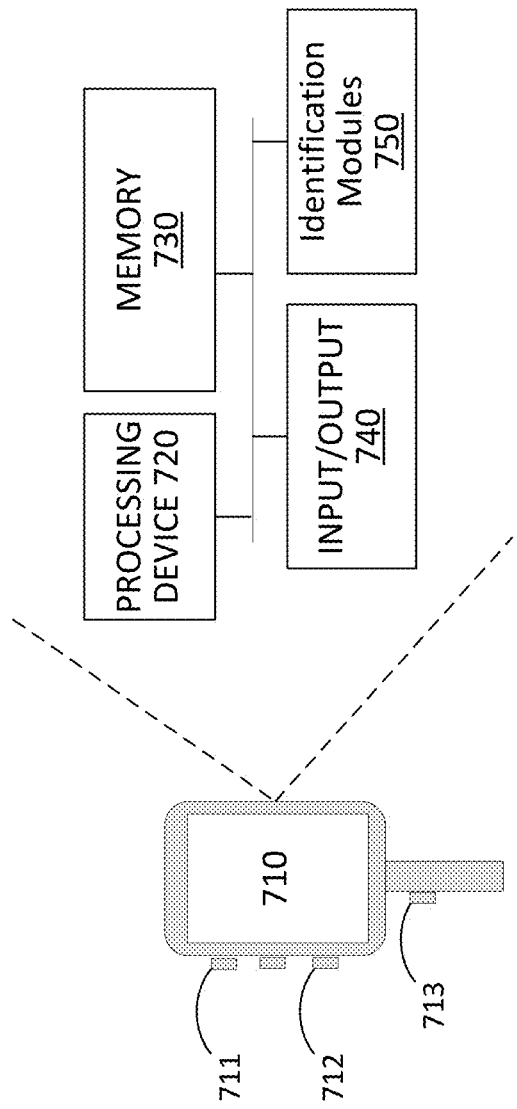

SYSTEMS AND METHODS FOR REMOTE IDENTIFICATION

BACKGROUND OF THE INVENTION

Field of the Invention

The present disclosure generally relates to identification devices, and more particularly, to systems and methods that identify an individual and/or an object from a remote and adjustable distance.

Discussion of the Related Art

Identification devices, such as wearable wristbands, have long been used to identify individuals in particular settings. One common use is to identify patients within hospitals, out-patient clinics, and the like. When used in combination with an appropriate reading device, such as a bar code or radio frequency identification (RFID) scanner, a patient can be accurately identified so that appropriate test(s) can be performed, drugs administered, and the like.

FIG. 1 illustrates an identification device according to the prior art. The identification device 100 includes substrate 110, identification mechanism 120, and snap fastener components 132, 134, and 136 (collectively, fastener 130). Here, the substrate 110 forms an elongated flexible strip that may be worn as a patient wristband. Coupled to the substrate 110, the identification mechanism 120 may include a bar code or radio frequency identification (RFID) circuit. Fastener 130 is configured to adjustably and securely attach the identification device 100 to the wrist of a patient.

Unfortunately, existing identification devices, such as the identification device 100, only interface with corresponding reading devices at close range (i.e., typically less than three inches). In addition, conventional identification devices require direct line of sight to be read. As a result, reading of a conventional identification device frequently requires disruption of the patient. For example, blankets may need to be removed from a sleeping patient in order to read a wearable band. In another example, a new born child may need to be removed from an incubator in order to determine the infant's identity.

In light of the problems identified above, the inventor has provided systems and methods for more effectively identifying an individual and/or an object from a remote and adjustable distance.

SUMMARY OF THE INVENTION

Embodiments of the present invention are directed to systems and methods for identifying an individual and/or an object from a remote and adjustable distance that substantially address or obviate one or more limitations or disadvantages of the related art. Features and advantages of the invention are set forth in the description which follows, or will be apparent from the description, or may be learned by practice of the invention.

In an example embodiment, the systems and methods for exchanging identification data between an identification device and a bidirectional device include receiving, at the identification device, a request for identification data from the second device, retrieving, at the identification device, the requested identification data and supplemental data associated with the identification data, and transmitting, within an ultra-high frequency range, a radio frequency identification tag containing the requested identification data and the supplemental data to the bidirectional device. In some instances, the bidirectional device also may write supplemental data to the identification device.

In another example, the bidirectional device may be configured to receive identification and supplemental data from the identification device from a remote distance of at least 18 inches. In addition, the communication distance range between the identification device and the bidirectional device may be adjustable. Alternatively, or additionally, the communication frequency between the identification device and the bidirectional device may be adjustable.

In another example, the identification device may be composed of a multilayer structure and include identification circuitry in an inner layer.

In yet another example, the supplemental information may include biometric information such as patient allergies, blood type, medical conditions, medication dosages, and the like.

In yet another example, the information stored within the identification device may be modified by a remote bidirectional device.

It is to be understood that both the foregoing general description and the following detailed description are exemplary and explanatory and are not intended to limit the invention to the described examples.

BRIEF DESCRIPTION OF THE DRAWINGS

The accompanying drawings, which are included to provide a further understanding of the disclosure and are incorporated in and constitute a part of this specification, illustrate embodiments of the disclosure and together with the description serve to explain the principles of the disclosure.

FIG. 2 illustrates an identification device according to an example embodiment of the present invention.

FIG. 3 illustrates a cross-sectional view of the identification device according to an example embodiment of the present invention.

FIG. 6 is a block diagram illustrating identification circuitry of the identification device according to an example embodiment of the present invention.

FIG. 7 illustrates a representative architecture of a bidirectional device according to an example embodiment of the present invention.

DETAILED DESCRIPTION OF THE INVENTION

Figure 1:
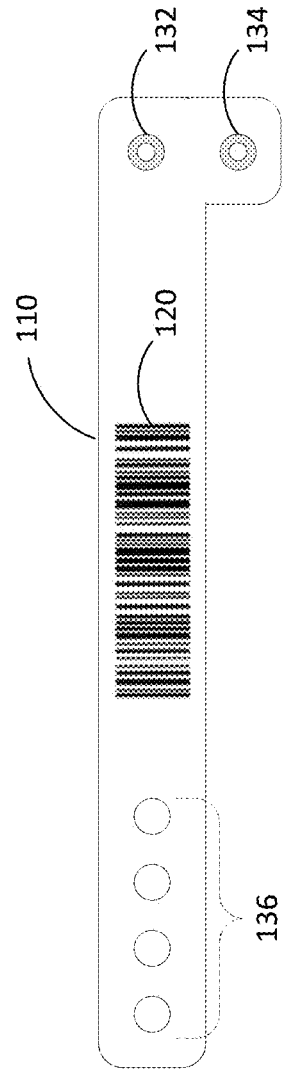
FIG. 1 illustrates an identification device according to the prior art.

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, and circuits have not been described in detail so as not to unnecessarily obscure aspects of the embodiments. Wherever possible, like reference numbers will be used for like elements.

Embodiments of the invention are generally directed toward improved systems and methods for identifying an individual and/or an object from a remote and adjustable distance. In particular, the example embodiments exchange identification data between an identification device and a bidirectional device. At the outset, the identification device may receive a request for identification data from the bidirectional device. In response to the request, the identification device may retrieve the requested identification data as well as supplemental data associated with the identification data. After retrieval, the identification device may transmit, within an ultra-high frequency range, a radio frequency identification tag containing the requested identification data and the supplemental data to the bidirectional device.

Although a wearable band is described and illustrated, the embodiments are not so limited. The improved identification device may include an adhesive label or patch, anklet, bracelet, finger band (i.e., ring), headband, identification card, necklace, waistband, wristband, or other wearable appliance, which for the sake of convenience, are collectively referred to as an "identification device."

FIG. 2 illustrates an identification device according to an example embodiment of the present invention. As illustrated by FIG. 2, the identification device 200 includes substrate 210, identification circuitry 220, and fastener components 232, 234, and 236 (collectively, fastener 230).

In the example identification device 200, the substrate 210 forms an elongated flexible strip that may be a wearable band, such as a patient wristband. As will be discussed in detail in connection with FIG. 3, the substrate 210 may include a plurality of layers. For example, the multi-layer substrate may include one or more polypropylene film(s), such as bi-oriented polypropylene (BOPP); thermal sensitive layer(s) including a polymeric binder, a sensitizer, a developer and/or a leuco dye coated directly on a base material; primer layer(s) including a water soluble polymer coated directly onto the thermal sensitive layer; heat resistant layer(s) including a cross-linked, photo polymerized acrylic polymer coated onto the primer layer; a circuitry inlay later; hypoallergenic adhesive(s) such as acrylate which is designed for medical and surgical applications; and/or contact layer(s) including hypoallergenic and/or hydrophobic materials designed for direct skin contact in medical and surgical applications.

In selecting materials, various factors may be considered. For example, a wristband for use in a hospital setting will likely be comprised of hypoallergenic materials that are compatible with sterilization techniques (e.g., Ethylene Oxide (EtO), gamma, and/or other sterilization methods). In another example, flexible, soft, and/or comfortable materials may be desired, especially for certain groups of individuals (e.g., infants, children, elderly, sensitive persons, etc.). Other considerations may also include the color of the material, especially when text, such as a patient name, may be printed on the identification device 200.

The identification circuitry 220 may include an ultrahigh frequency (UHF) radio frequency identification (RFID) circuit. Within a circuitry inlay layer of the substrate 210, identification circuitry 220 may be provided. Identification circuitry 220 may be configured to store identification information (e.g., patient name, object name, identification number, birth date, and the like) and/or other information regarding an associated object or wearer. For example, biometric data (e.g., patient allergies, blood type, medical conditions, medications and dosages, medical records, and the like) may be provided. Such information may be stored within a memory of the identification circuitry 220, and may be wirelessly communicated to an associated bidirectional device. For example, read/write functions of an RFID tag may be executed from anywhere within range of a bidirectional device. In another example, a bidirectional device may be configured to write identification and/or supplemental information to the identification circuitry 220.

The identification circuitry 220 may emit a passive RFID tag within the UHF range. For example, a passive RFID tag may be emitted within a frequency range of 30 Megahertz (MHz) to 300 Gigahertz (GHz). In some embodiments, it may be preferred to emit RFID tags within a narrower frequency band, such as 860 MHz to 960 MHz. As compared to conventional identification devices, the UHF RFID circuit described herein is particularly advantageous. By using a UHF RFID circuit, an associated bidirectional device may transmit and receive information with identification device 200 from a remote distance. Using UHF, a scanning device may communicate with an identification device 200 from a distance of up to 30 feet. Within a hospital setting, the UHF RFID circuit may be configured to communicate within a smaller distance (e.g., 18 inches). Moreover, line of sight is not required between identification device 200 and an associated bidirectional device.

In some embodiments, the communication distance of the bidirectional device may be adjustable. Alternatively, the range of a passive RFID tag may be varied. In yet another alternative, the frequency within the UHF range may be varied. For example, identification circuitry 220 may be configured to emit a passive RFID tag at one or more frequencies, each frequency having different signal strengths so as to be read at varying distances. In either case, a passive RFID tag emitted by identification circuitry may be read from any distance within range of the bidirectional device. Accordingly, the communication requirements of a variety of environments may be satisfied.

Example fastener 230 is configured to adjustably and securely attach the identification device 200 to the wrist of the patient. As depicted, the fastener 230 includes first and second connectors 232 and 234 that cooperate with each other to form an interlocking mechanism. For example, first and second connectors 232 and 234 may fold over the other end of identification device 200 through one of the adjusting holes 236 and snap together.

Although a snap-type configuration is shown, other fastener types may be used. For example, adhesive, crimp, heat-created, latch, magnetic, plug, rivet, screw, staple, track, and other connector mechanisms types may be used to ensure that the identification device 200 is securely attached to an individual or object.

Accordingly, use of identification device 200 enables efficient identification of patients without moving or adjusting the patient to scan a barcode or prior art RFID. The identification device 200 also enables patient information to be collected from a remote distance through blankets and clothing using UHF RFID bidirectional devices and the improved identification device 200. In addition, the identification device 200 may be used with other identification mechanisms, such as one and two dimension bar codes, human-readable text, and the like.

FIG. 3 illustrates a cross-sectional view of the identification device 300 according to an example embodiment of the present invention. The identification device 300 may be composed of a multilayer structure having layers 310, 320, 330, 340, 350, and 360. The cross-sectional view illustrates multiple layers 310-360 along a cross-section line A-A' shown in FIG. 2.

Referring back to FIG. 3, polypropylene layer 310 may include one or more sub-layers comprised of polypropylene film(s), such as bi-oriented polypropylene (BOPP). Here, the polypropylene layer 310 may have varying thicknesses of up to 6 mm, preferable 4-6 mm.

Thermal sensitive layer 320 may include one or more sub-layer(s) comprised of a polymeric binder, a sensitizer, a developer and/or a leuco dye. In some embodiments, the density of the thermal sensitive layer 320 may vary, but is typically on the order of 4 $g/m^2$.

Primer layer 330 may include one or more sub-layer(s) comprised of a water soluble polymer. The primer layer may be coated directly onto the thermal sensitive layer 320. In some embodiments, the density of the primer layer 330 may vary, but is typically on the order of 2 $g/m^2$.

Heat resistant coating layer 340 may include one or more sub-layer(s). For example, the heat resistant coating layer 340 may be comprised of a cross-linked, photo polymerized acrylic polymer. In addition, the heat resistant coating layer 340 may be coated directly onto the primer layer 330.

Circuitry inlay layer 350 may include one or more sub-layer(s) of insulating materials. Here, the identifying circuitry 220, including processing logic and/or antenna(s), may include one or more of conductive paths, semiconductor device(s), and/or polymer material(s). The various components of the identifying circuitry may be deposited on the circuitry inlay layer 350. Subsequently, the circuitry inlay layer 350 may be coupled to the heat resistant coating layer 340 and contact layer 360.

Lastly, contact layer 360 may include various hypoallergenic and/or hydrophobic materials designed for direct skin contact in medical and surgical applications. Alternatively, contact layer 360 may include an adhesive so as to be coupled to a receiving patient or object (e.g., patch or sticker). In addition, hypoallergenic adhesive(s), such as acrylate which is designed for medical and surgical applications, may be used throughout multi-layer substrate.

Figure 4A:
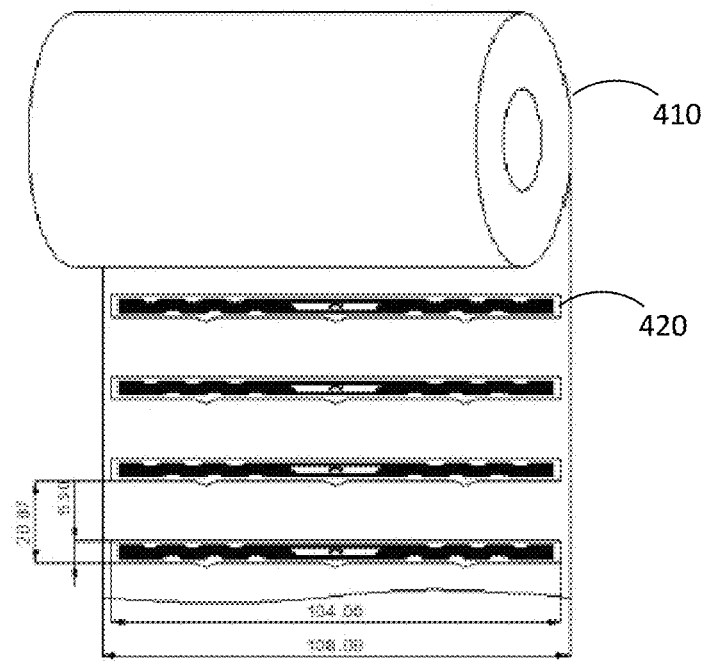
FIGS. 4A and 4B are representative illustrations of an example method of depositing identification circuitry to an identification device.
Figure 4B:
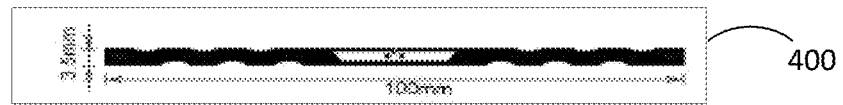

FIGS. 4A and 4B are representative illustrations of an example method of depositing identification circuitry 420 to an identification device 400. A substrate sheet 410 is supplied to a depositing device (not shown), and a plurality of individual identification circuitry units 420 is deposited onto a substrate sheet 410. Subsequently, additional layers may be deposited onto the substrate sheet 410 so as to produce a multi-layer structure as shown in FIG. 3. Lastly, the substrate sheet is divided into a plurality of identification devices 400, as shown in FIG. 4B. Of course, other manufacturing processes, such as wet inlay methods, known to those of skill in the art of making devices may be used, as needed.

Figure 5:
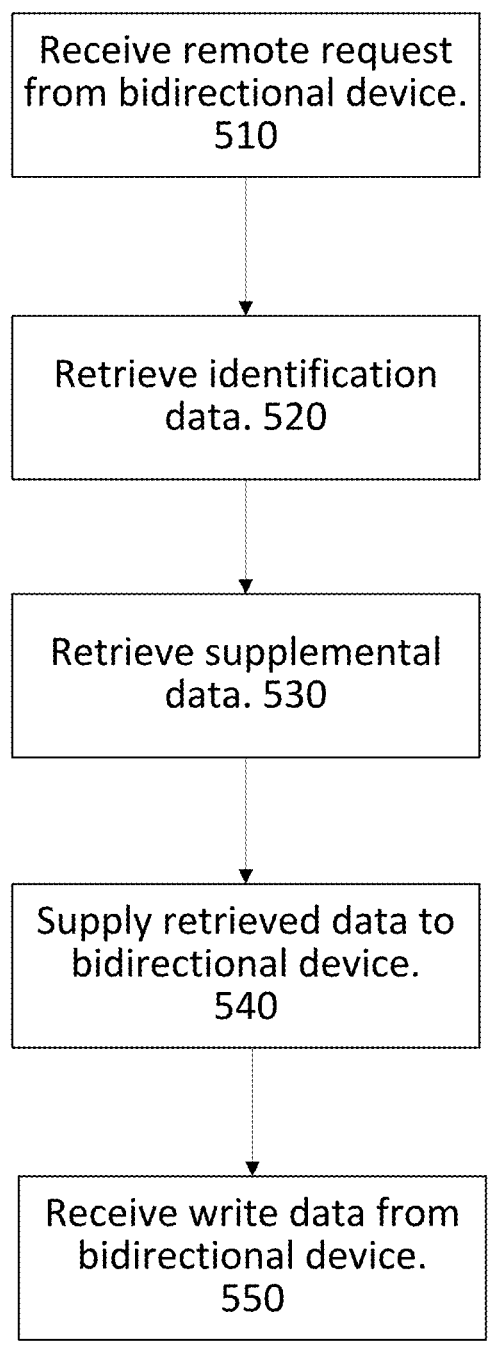
FIG. 5 illustrates a method, implemented by an identification device, for processing a request from a bidirectional device according to an example embodiment.

FIG. 5 illustrates a method 500, implemented by an identification device, for processing a request from a bidirectional device according to an example embodiment. At the outset, the identification device may receive a request for identification data from the bidirectional device, at 510. In response to the request, the identification device may retrieve the requested identification data as well as supplemental data associated with the identification data, at 520 and 530. Here, the supplemental information may include biometric information such as patient allergies, blood type, medical conditions, medication dosages, and the like. After retrieval, the identification device may transmit, within an ultra-high frequency range, a radio frequency identification tag containing the requested identification data as well as the supplemental data to the bidirectional device, at 540. Additionally, the bi-directional device may write and/or modify the identification and/or supplemental data stored at the identification device, at 550. For example, if a patient is determined to have a new allergy, such information may be added to the patients supplemental data stored on the identification device. In another example, if a patient undergoes a series of treatments (e.g., treatment protocol), the bidirectional device may add workflow data such that identification device may track the completion of each treatment.

Although not shown, a bidirectional device may include a security mechanism, such as a password, such that only authorized users may access information stored on the identification device. For example, such security measures may be implemented on an individualized or group basis.

FIG. 6 is a block diagram illustrating identification circuitry 620 of the identification device 600 according to an example embodiment of the present invention. As shown in FIG. 6, the identification circuitry 620 may include a memory 621, printed circuitry components 622, and antenna 623.

Memory 621 may be configured to store identification information as well as other associated information. For example, memory 621 may store patient identity information as well as biometric data such as patient allergies, blood type, medical conditions, medications and dosages, and the like. Such information may be retrieved by circuit components 622 and wirelessly transmitted to an associated bidirectional device via antenna 623. For example, such information may be incorporated into a passive RFID tag such that it may be received by a nearby bidirectional device.

FIG. 7 is a system diagram illustrating bidirectional device according to an example embodiment of the present invention. The example bidirectional device 700 may include display 710, processing device 720, memory 730, and input/output module(s) 740. Components of the bidirectional device 700, such as display 710, processing device 720, memory 730, and communications device 740, may be interconnected via a system bus.

Bidirectional device 700 may also include one or more identification module(s) 750 and/or other modules or components that generally implement the functionality of the bidirectional device. The components and functions of the information module(s) 750 are explained in detail with reference to FIGS. 2, 3, and 5. Also, processing device 720 may execute instructions of the information module(s) 750 as well as other modules stored in memory 730.

As shown, the bidirectional device 700 may include one or more user-adjustable input devices 711, 712, and 713. Input devices 711-713 may be implemented as press-able buttons, rotatable knobs, slide-able latches, and the like. Alternatively, such input devices may be manipulated through an electronic menu of the identification module(s) 750 that may be depicted on display 710. In addition, input devices 711-713 may be configured to control the operation of the bidirectional device 700. For example, the communication distance of the bidirectional device 700 may be adjustable by input device 711. In another example, the range of frequencies scanned by the bidirectional device 700 may be varied by input device 712. Alternatively, settings (e.g., communication distance, frequency, data field configuration, and the like) of the bidirectional device 700 may be stored on a removable nonvolatile memory card (e.g., secure digital (SD) card) that is locally or remotely programmed. Here, the bidirectional device 700 may be programmed using a configuration utility that may be accessed using a USB cable or wireless connection, or by reprogramming the memory card at a computer hosting the configuration utility. In yet another example, activation of the input device 713 may cause information from a near-by identification device to be depicted on display 710. Here, a single activation of input device 713 may retrieve identification information, and a second activation may further retrieve associated information.

Memory 730 may include a non-transitory computer readable medium configured to store information module(s). In an example embodiment, memory 730 may contain different components for retrieving, presenting, changing, and saving data and may include computer readable media. Memory 730 may include a variety of memory devices, for example, Dynamic Random Access Memory (DRAM), Static RAM (SRAM), flash memory, cache memory, and other memory devices. Additionally, for example, memory 730 and processing device(s) 720 may be distributed across several different computers that collectively comprise a system.

In some instances, the bidirectional device 700 may be wirelessly coupled (e.g., Bluetooth) to a remote computer that stores and/or displays data such as patient information (e.g., patient name, object name, identification number, birth date, patient allergies, blood type, medical conditions, medications and dosages, medical records, and the like). Alternatively, the bidirectional device 700 may further include a removable memory card to easily store large amounts of information, such as patient data.

Communications device 740 may enable connectivity between the processing devices 720 in the bidirectional device 700 and other systems by encoding data to be sent from the processing device 720 to another system over a network and decoding data received from another system over the network for the processing device 720. In various embodiments, the bidirectional device 700 may have an architecture with modular hardware and/or software systems that include additional and/or different systems communicating through one or more networks via communications device 740.

Processing device 720 may perform computation and control functions of a system and comprises a suitable central processing unit (CPU). Processing device 720 may include a single integrated circuit, such as a micro processing device, or may include any suitable number of integrated circuit devices and/or circuit boards working in cooperation to accomplish the functions of a processing device. Processing device 720 may execute computer programs, such as object-oriented computer programs, within memory 730.

In some configurations, the bidirectional device 700 may be physically and electrically coupled to a mobile computing device (e.g., smartphone or tablet) such that information may be stored and/or displayed on the mobile computing device. By mounting the mobile computing device, the bidirectional device 700 may rely upon the display, communication, processing, and memory functions of the mobile computing device in order to implement its functions. Additionally, an application residing on the mobile computing device may be configured to cooperate with user-adjustable input devices 711, 712, and 713.

With respect to the depicted system configurations depicted, it should be appreciated that in other embodiments, the systems and network configurations may include fewer or more components apart from those shown. The components and respective modules may be in the form of software that is processed by a processor. In another example, the components and respective modules may be in the form of firmware that is processed by application specific integrated circuits (ASIC), which may be integrated into a circuit board. The components and respective modules also may be in the form of one or more logic blocks included in a programmable logic device (for example, a field programmable gate array). The components and respective modules may be adapted, and/or additional structures may be provided, to provide alternative or additional functionalities beyond those specifically discussed.

It will be apparent to those skilled in the art that various modifications and variations can be made in the systems and methods for remote identification the present disclosure without departing from the spirit or scope of the disclosure. Thus, it is intended that the present disclosure cover the modifications and variations of this disclosure provided they come within the scope of the appended claims and their equivalents.

What is claimed is:

1. A method for exchanging identification data between a patient identification device and a bidirectional device, the method comprising:
   receiving, at the patient identification device, a request for identification data from the bidirectional device;
   retrieving, at the patient identification device, the requested identification data and supplemental data associated with the identification data; and
   transmitting, within an ultra-high frequency range, a radio frequency identification tag containing the requested identification data and the supplemental data to the bidirectional device.

2. The method according to claim 1, wherein the patient identification device is a UHF RFID patient identification wristband.

3. The method according to claim 1, wherein the bidirectional device is an ultra-high frequency bidirectional device.

4. The method according to claim 1, wherein the bidirectional device receives identification data from the patient identification device from a distance of at least 18 inches.

5. The method according to claim 1, wherein the patient identification device is composed of a multilayer structure and includes identification circuitry in an inner layer.

6. The method according to claim 1, wherein the supplemental information includes biometric information.

7. The method according to claim 1, wherein the supplemental information includes at least one of patient allergies, blood type, medical conditions, medication dosages, and medical records.

8. The method according to claim 1, wherein the communication distance range between the patient identification and bidirectional devices is adjustable by the bidirectional device.

9. The method according to claim 1, wherein the communication frequency between the patient identification and bidirectional devices is adjustable by the bidirectional device.

10. A non-transitory computer readable storage medium storing one or more programs configured to be executed by a processor, the one or more programs for exchanging data between a patient identification device and a bidirectional device, and comprising instructions for:
   receiving, at the patient identification device, a request for identification data from the bidirectional device;
   retrieving, at the patient identification device, the requested identification data and supplemental data associated with the identification data; and
   transmitting, within an ultra-high frequency range, a radio frequency identification tag containing the requested identification data and the supplemental data to the bidirectional device.

11. The computer readable storage medium according to claim 10, wherein the patient identification device is a patient identification wristband.

12. The computer readable storage medium according to claim 10, wherein the bidirectional device is an ultra-high frequency bidirectional device.

13. The computer readable storage medium according to claim 10, wherein the bidirectional device receives identification data from the patient identification device from a distance of at least 18 inches.

14. The computer readable storage medium according to claim 10, wherein the patient identification device is composed of a multilayer structure and includes identification circuitry in an inner layer.

15. The computer readable storage medium according to claim 10, wherein the supplemental information includes biometric information.

16. The computer readable storage medium according to claim 10, wherein supplemental information includes at least one of patient allergies, blood type, medical conditions, medication dosages, and medical records.

17. The computer readable storage medium according to claim 10, wherein the communication distance range between the patient identification and bidirectional devices is adjustable by the bidirectional device.

18. The computer readable storage medium according to claim 10, wherein the communication frequency between the patient identification and bidirectional devices is adjustable by the bidirectional device.

19. A communications device comprising:
one or more processors; and
memory storing one or more programs for exchanging data between the communication device and a bidirectional device, and comprising instructions for execution by the one or more processors, the one or more programs including instructions for:
receiving, at the communications device, a request for identification data from the bidirectional device;
retrieving, at the communications device, the requested identification data and supplemental data associated with the identification data; and
transmitting, within an ultra-high frequency range, a radio frequency identification tag containing the requested identification data and the supplemental data to the bidirectional device.

20. The communications device according to claim 19, wherein the communications device is a patient identification wristband.

21. The communications device according to claim 19, wherein the bidirectional device is an ultra-high frequency bidirectional device.

22. The communications device according to claim 19, wherein the bidirectional device receives identification data from the communication device from a distance of at least 18 inches.

23. The communications device according to claim 19, wherein the communications device is composed of a multilayer structure and includes identification circuitry in an inner layer.

24. The communications device according to claim 19, wherein the supplemental information includes biometric information.

25. The communications device according to claim 19, wherein supplemental information includes at least one of patient allergies, blood type, medical conditions, medication dosages, and medical records.

26. The communications device according to claim 19, wherein the communication distance range between the communication and bidirectional devices is adjustable by the bidirectional device.

27. The communications device according to claim 19, wherein the communication frequency between the communication and bidirectional devices is adjustable by the bidirectional device.

* * * * *